US00PP21964P3

(12) United States Plant Patent

Felker et al.

(10) Patent No.: US PP21,964 P3

(45) Date of Patent: Jun. 7, 2011

(54) CACTUS PEAR PLANT NAMED 'DAR 1-29-21 GREEN'

(50) Latin Name: ***Opuntia ficus-indicia* L.**
Varietal Denomination: DAR 1-29-21 Green

(75) Inventors: Peter Felker, Salinas, CA (US); Ronald A Bunch, Salinas, CA (US)

(73) Assignee: D'Arrigo Bros. Co., of California, Salinas, CA (US)

( * ) Notice: Subject to any disclaimer, the term of this patent is extended or adjusted under 35 U.S.C. 154(b) by 13 days.

(21) Appl. No.: 12/584,814

(22) Filed: Sep. 14, 2009

(65) Prior Publication Data

US 2011/0067154 P1 Mar. 17, 2011

(51) Int. Cl.
*A01H 5/00* (2006.01)

(52) U.S. Cl. ..... Plt./156

(58) Field of Classification Search ..... Plt./372, Plt./156

See application file for complete search history.

(56) References Cited

OTHER PUBLICATIONS

Mondragon-Jacobo, C. And S. Perez-Gonzalez. 1996. "Native cultivars of cactus pear in México". p. 446-450. In: J. Janick (ed.), Progress in new crops. ASHS Press, Arlington, VA.*

Barbera et al.,1992 Physical, morphological and chemical changes during fruit development and ripening in three cultivars of prickly pear. J Hort Sci 67:307-312.

Felker et al., 2005.Comparison of *Opuntia ficus indica* varieties of Mexican and Argentine origin for fruit yield and quality in Argentina. J. Arid Env 60:405-422.

Mondragon and Gonzalez. 1994. Reyna (syn. Alfajayucan') is the leading cactus pear cultivar in Central Mexico. Fruit varieties journal. 48: 134-136.

Mondragon and Gonzalez. 1996. Native cultivars of cactus pears in Mexico. p. 446-450 In: J.Janick (ed), Progress in new crops. ASHS Press, Arlington, VA.

Mondragon. 2001.Verification of the Apomictic Origin of Cactus Pear (*Opuntia* spp) seedlings of OP and Crosses from Central Mexico. J. Prof Assn Cactus Dev 4: 49-56.

Nerd et al., 1991. Out of season prickly pear: fruit characteristics and effect of fertilization and short droughts on productivity. HortScience 26: 337-342.

Parish and Felker 1997.Fruit quality and production of cactus pear (*Opuntia* spp) clones selected for increased frost hardiness. Journal of Arid E.nvironments 37:123-143.

UPOV, 2006. Cactus pear and xoconostles. TG/217/2. International Union for the protection of new varieties of plants. Geneva.

Wang et al., 1996. Cross-hybridization and seed germination in *Opuntia* species. J. Prof Assn Cactus Dev 1:49-60.

* cited by examiner

*Primary Examiner* — Susan B McCormick Ewoldt

(57) ABSTRACT

A new and distinct variety of cactus pear having the following unique combination of desirable features:

1. A fruit with a green colored edible interior portion.
2. An average Brix of 14.6%.
3. An average firmness of the pulp of 2.9 lb.
4. An average pulp percentage of 50%.
5. A fruit weight ranging from 130 to 170 g.
6. Cladodes that have a low percentage of areoles with spines and those areoles only have 1 spine per areole of maximum length of 8 mm.
7. Greater resistance to water soaked, translucent aspect of edible fruit portion from rapid increases in temperature known as clearing than other *Opuntia ficus indica* with green fruits.

5 Drawing Sheets

Latin name of the genus and species claimed: *Opuntia ficus-indica* L. Miller.

Variety denomination: 'DAR 1-29-21 Green'.

BACKGROUND OF THE INVENTION

Fruits of spiny and spineless *Opuntia ficus indica* are about 110-180 grams, range from 12 to 15% total soluble solids (Brix), have a variety of fruit colors, i.e. green, orange, red and purple, and have been grown in many arid regions of the world such as Mexico, Brazil, Chile, Argentina, Spain, Italy, Israel, South Africa for commercial fruit production (Parish and Felker, 1997). Mexico is the world center of production with great variation in spines, fruit colors, dates of maturity and Brix (Mondragon and Gonzalez, 1996). While the lime green variety Reyna is the leading cactus pear variety in Mexico (Mondragon and Gonzalez, 1994), this variety has long spines that prevent its cultivation in the USA due to objections from harvesting crews. Mondragon and Gonzalez, (1996) have reported fruits of many colors, but they have not provided experimental details on field design, laboratory methods or coefficients of variation for these properties and they do not provide data on firmness of the edible inner portion which Felker et al., (2005) have suggested needs to be greater than 2.2 lb for a good quality fruit. Moreover data on fruit Brix, firmness, weight, peel thickness, percentage of edible portion on more than 30,000 fruit of existing varieties and progeny of new crosses is not in agreement with Brix values of 15-16 for red or purple colored fruits reported by Mondragon and Gonzalez, (1996). *Opuntia* fruit data from refereed journal articles in which field and laboratory experimental details with estimates of the variation, have been provided by Barbera et al., (1992), Nerd et al., (1991) and Felker et al., (2005).

In 1998, obtained copies of the more than 100 *Opuntia* clones from Kingsville Tex. (that were later deposited in the USDA *Opuntia* germplasm collection in Parlier, Calif.) that represented all of the major types present in Mexico, South Africa, Argentina and Chile. As described below, as none of the existing cultivars met objectives of high pulp firmness (>2.8 lb), high Brix (>14), thornlessness, lime green color and low damage from rapid temperature changes known as clearing, hybridizations were conducted to obtain the desired variety.

There are extensive plantations of cactus pear for fruit in the Mediterranean, principally Sicily but also Spain and Israel. *Opuntia ficus indica* was brought to Spain on one of the first voyages of Christopher Columbus from where it spread to the rest of the Mediterranean region. In the largest commercial production area of the Mediterranean in Sicily, there are 3 varieties, 'Rossa' (with red fruit), 'Gialla' (with yellow fruit) and 'Bianca' (with almost colorless fruit) (Barbera et al., 1992). These three varieties were essentially the same with regard to fruit quality with a maximum Brix of about 13% (Barbera et al., 1992). Nerd et al., (1991) in Israel, found the Brix of the summer 'Ofer' variety (which is yellow and similar to the 'Gialla' from Sicily) to be 11.8% in the winter and 12.8% in the summer. In Argentinean field trials, the Kingsville, Tex. (TAMUK) accession 1281 (which is very similar to the Italian 'Rossa'), and TAMUK 1277 and 1320 (which are similar to Italian 'Gialla') had Brix values of about 12.6, 12.7 and 13.0 respectively (Felker et al., 2005).

In spite of acceptable fruit sugar concentrations of about 13% in high yielding varieties, such as Italian 'Rossa' and 'Gialla' types (including 1281, 1277, 1320), these varieties have very low pulp firmness of about 2 lb (versus 4 lb for spiny orange 1287 and green fruited Argentine and Chilean varieties) which lead to poor consumer acceptance in Argentina (Felker et al., 2005). While firmness is the parameter measured, the objectionable quality is that pulps with low firmness value lack structural integrity and may break apart when the peel is separated from the pulp. A pulp firmness of about 2.2 lb has been suggested as the minimum acceptable for cactus fruit (Felker et al., 2005).

In the USA, the only commercial variety, the 'Andyboy Red', is similar to the Italian 'Rossa'. The 'Andyboy Red' has a Brix of about 13.5 in the summer crop but maybe as low as 10.5 in the mid winter crop. Perhaps due to the cooler weather of the growing region in the USA, the red fruits do not break apart when peeled, but they are not as firm and juicy as other types. The 'Andyboy Red' is also in the low range of pulp firmness of about 2 lb. In the USA, the major demand from consumers is for the red colored fruit.

In spite of the lack of red color, the nearly 2% increase in Brix (from about 12.7 to 14.6) and the greater firmness and juiciness of cactus fruits with a lime green interior are much appreciated by many consumers. The lime green fruits have two shortcomings when grown along the California Pacific coast. First short periods of higher than normal daily maximum temperature causes the edible portion of the fruit to have a water soaked, translucent appearance and an off flavor (called clearing). Secondly the edible fruit portion of green fruit has a much lower percentage than that of the red fruited varieties.

Therefore using the basic crossing technique of Wang et al., (1996), hybrids were made between parents that were thorny, high firmness, high Brix fruits with low clearing and a high pulp/peel ratio and parents that were thornless, high firmness, low pulp %, high susceptibility to fruit clearing, to develop a high Brix, high firmness, and thornless green fruited variety with improved pulp %, reduced clearing and good commercial yield. Progeny of the crosses were planted near Chualar, Calif. and evaluated for Brix and firmness using previously described techniques (Felker et al., 2005). After evaluating fruit data from hundreds of fruits from un replicated progeny in the field, about a dozen clones of green parents and the best of their progeny, were selected and planted in a randomized complete block trial with four replicates (with one plant per replicate) to directly compare fruit characters for these advanced selections. For two years, several fruits were taken from each of the four replicates, once a month from about September till May. The best green fruited variety of this randomized complete block trial, originally from Block 1, row 29 plant 21 of this trial was found to have the best overall combination of characters and is the subject of this patent. The parents of this plant were a spineless green variety with high clearing R7-54:1-08-43 and a spiny green variety with no clearing R7-53YT:1-01-12. None of the parents have been patented or have patent pending.

Asexual propagation

All cactus pear varieties are asexually propagated by cutting an approximate one year old cladode from the mother plant, allowing the cut scar to heal over for approximately 2 weeks and then planting this unrooted cladode (botanically a portion of a dicot stem) about ⅓ of its height into dry soil. If the cladode does not rot, 100% of them will root in less than a month without any hormone treatments Apomixis, that is the asexual reproductive process that occurs in the ovule of flowering plants, frequently occurs in *Opuntia ficus indica* (Mondragon-Jacobo, 2001). While the ratio of apomictic seedlings to seedlings resulting from fertilization varies greatly among female parents, we have found that apomixis occurs in this new variety. Thus this variety could be propagated asexually from apomictic seedlings. It is envisioned that this variety could be genetically engineered to include other traits.

This variety is propagated asexually by planting unrooted cladodes. The claimed plant retains its distinctive characteristics and reproduces true to type in successive generations.

BRIEF SUMMARY OF THE INVENTION

This invention relates to controlled hybridization to produce green cactus pears without spines and with significantly greater pulp percentages and resistance to clearing (heat damage) than other green cactus pears.

DETAILED BOTANICAL DESCRIPTION

Figure 1:
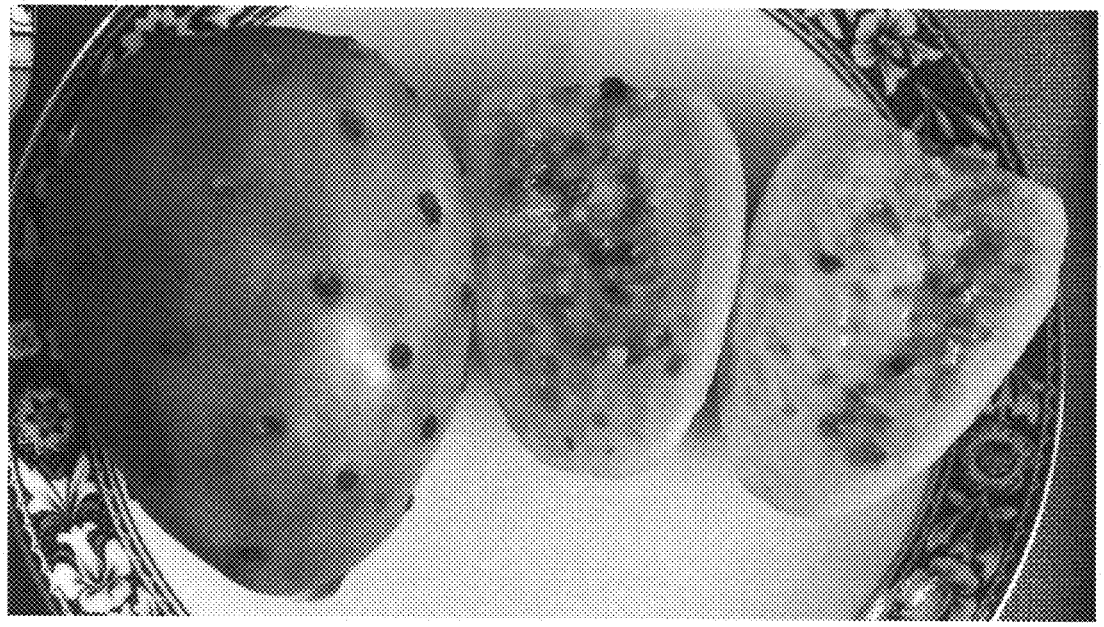
In FIG. 1 can be seen the exterior and interior portions of mature fruits of 'DAR 1-29-21 Green' at optimal harvest conditions after the spines and glochids removed. The interior of the fruit, after the peel has been removed, is the edible portion.
Figure 2:
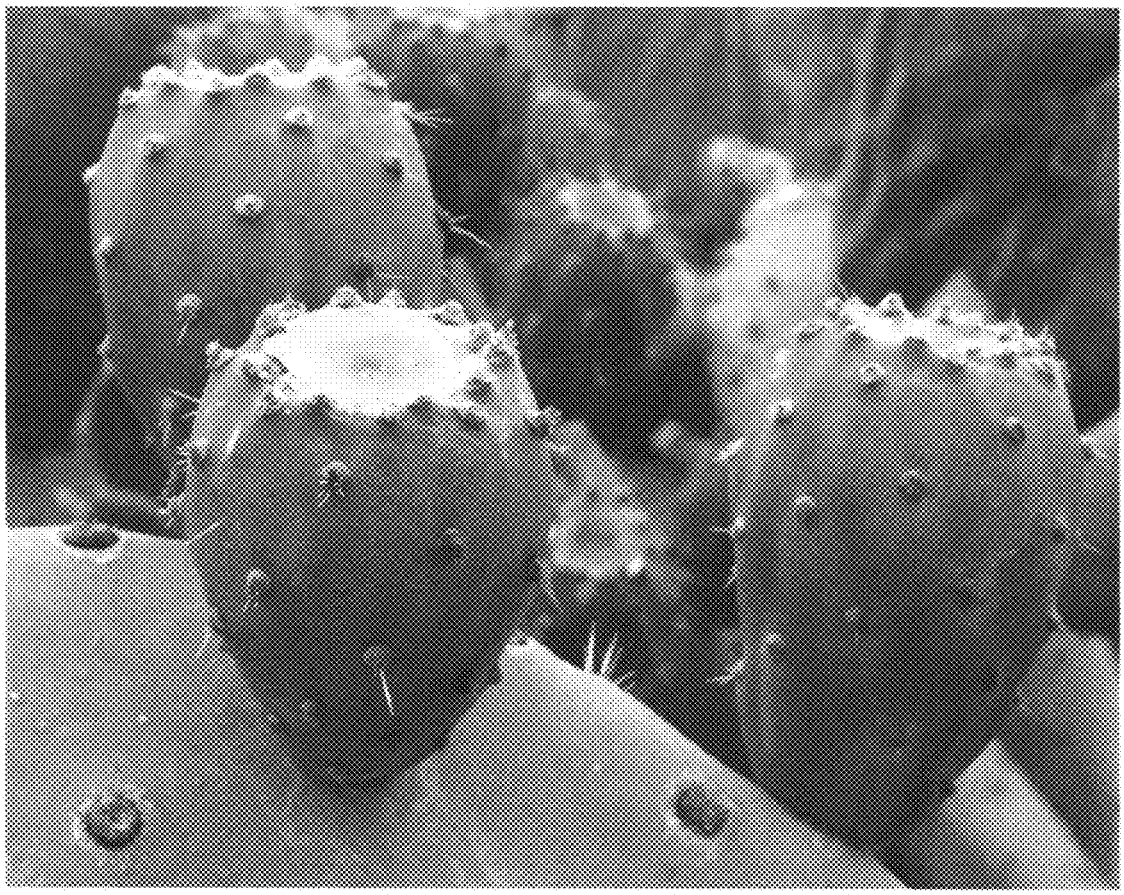
In FIG. 2 can be seen immature fruits of 'DAR 1-29-21 Green' showing the glochids.

The color chart used in this specification follows The Royal Horticultural Society Color Chart year 1996. The fruits have an obovate shape. At optimal harvest conditions, the external peel color ranges from 145A to 145 B and the internal edible portion ranges from 145A, 145B to 145C. In the winter this epidermal layer maybe reddish pink about 47C (but the underlying peel will be a light green). This variety should be harvested when the epidermal layer is no longer 100% green and shows at least about 25% yellowish color (155B) on the surface of the epidermis. There are about 36/37 areoles per fruit in which the number of glochids per areole greater than 2 mm in length is about 6. Due to the cool weather in the area where these fruits are grown, there are considerable glochids, especially on immature fruit as can be seen in FIG. 2. The fruit has no spines. The maximum glochid length is about 6 mm. There are less than about 100 glochids per areole. There is no pubescence. According to the UPOV classification, the stalk length is medium and the classification of the floral scar depression is 2. The peel thickness is about 9 mm.

Figure 3:
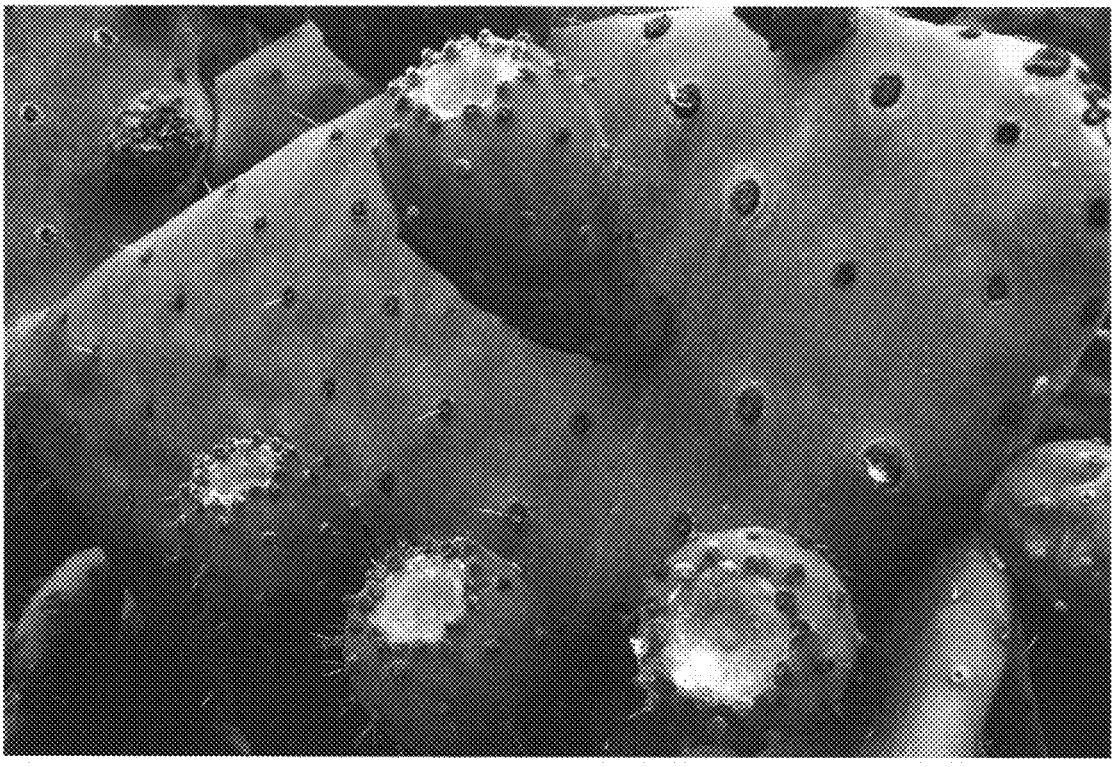
FIG. 3 illustrates a one year old cladode of 'DAR 1-29-21 Green' showing spines on the flat surface and margins of a cladode.
Figure 4:
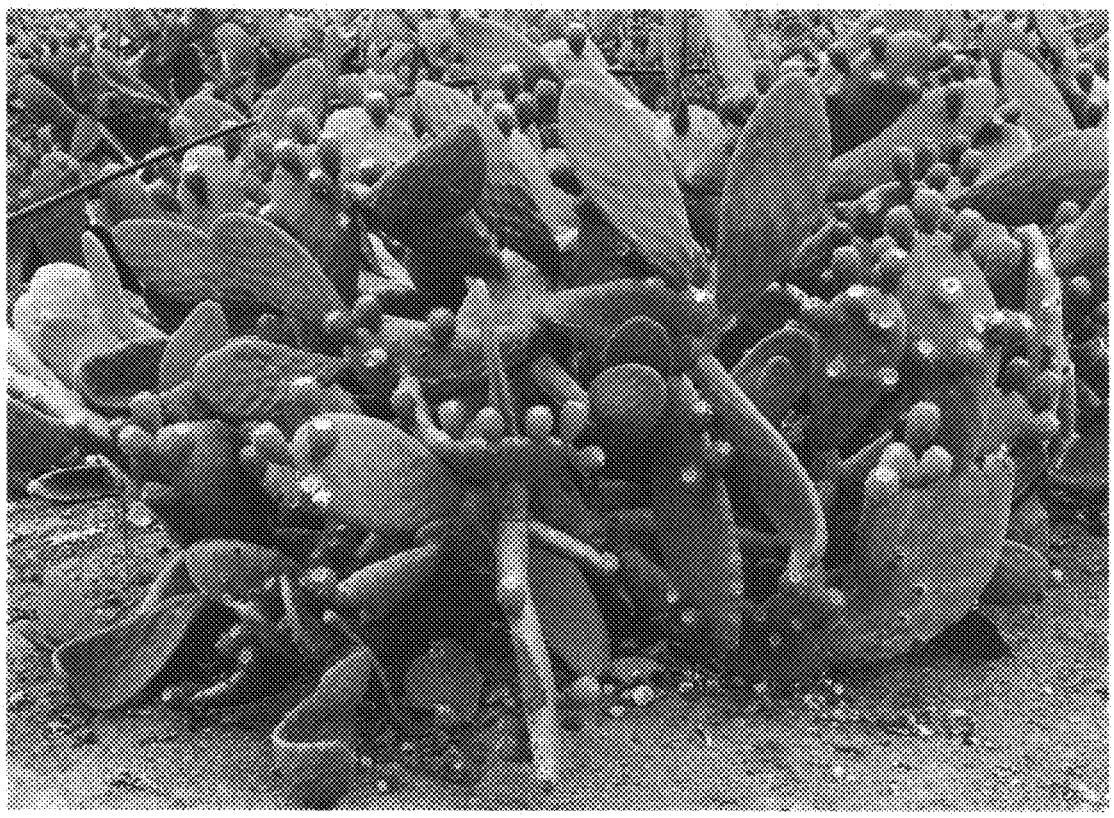
FIG. 4 shows a mature upright, three year old plant of 'DAR 1-29-21 Green' that was thinned to increase fruit size and pruned to keep the height low enough to pick the fruits.
Figure 5:
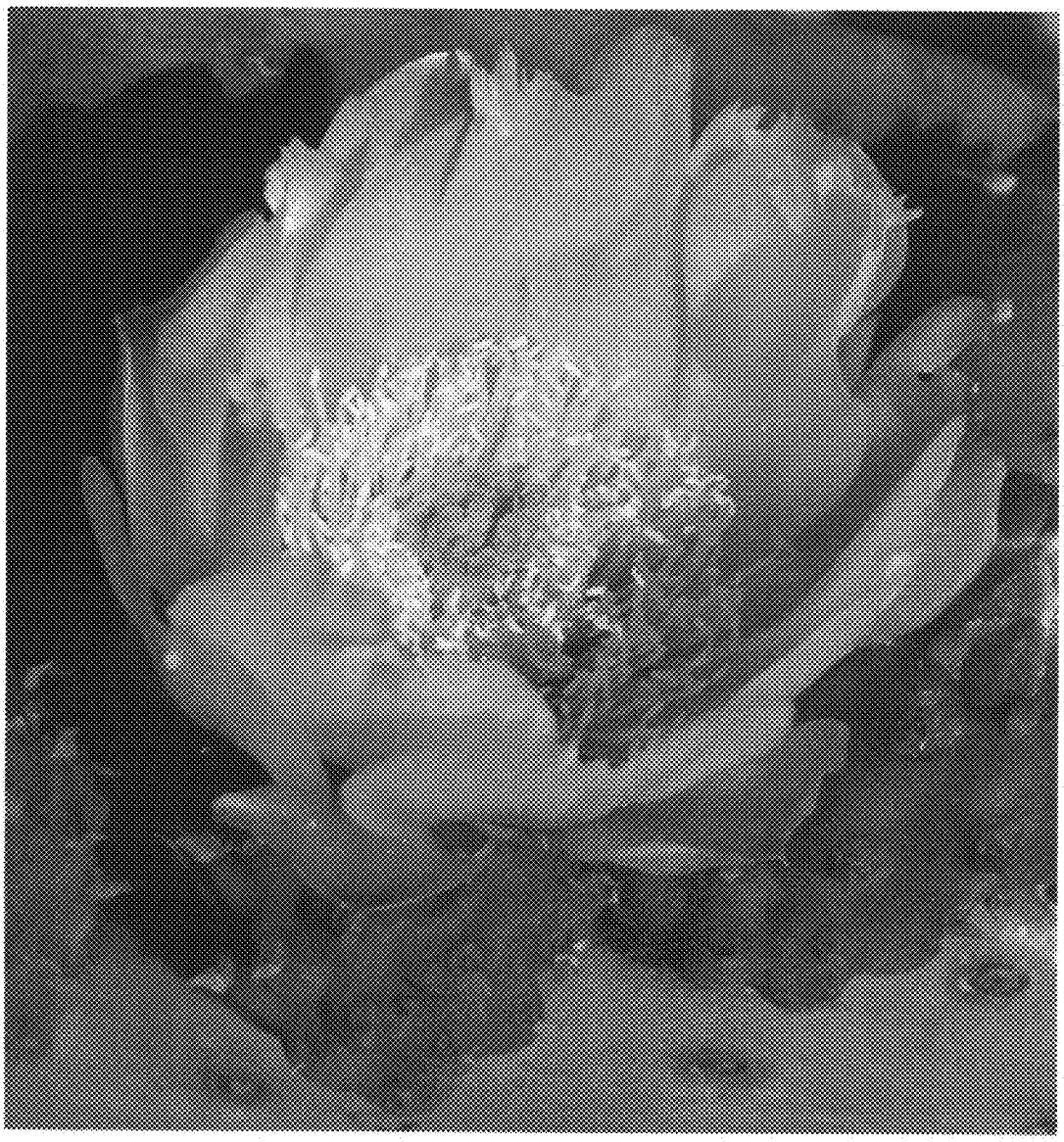
FIG. 5 shows an open flower of 'DAR 1-29-21' illustrating the petal color, stigma and dehiscing anthers.

This variety does not have multiple, long (3-5 cm) spines coming out from each areole of the cladodes as do *Opuntias* from the wild. However, as can be seen in FIG. 3, it does have single small semi erect spines of color 155D about 8 mm in length coming out some of the areoles. These spines occur most frequently on the margins of the cladode but can also be seen on the flat side of the cladodes. There are about 39 areoles per cladode with a color of 166A. The cladodes which have a color of 137C, have a smooth surface that is not waxy or pubescent. The sizes of the cladodes are greatly influenced by the climate and growing conditions. Nevertheless, near Gonzalez, Calif. where these plants are grown, a typical mature pad would have a medium elliptic shape and be about 45 cm long, 20 cm wide and 1.9 cm thick. A mature upright 3 year old plant, that is pruned to keep the height low enough to harvest fruits by hand, is about 3 meters wide and 1.7 m tall.

The flower diameter is about 6 cm and the length of the flower only (not including the immature supporting bud) is about 4 cm long. The length of supporting immature bud, when the flower is open, varies from about 3 cm to 6 cm depending on season of the year and moisture/fertility conditions. The flowers lack fragrance. The color of the broad elliptic shaped petals is 7A. Only one stigma, with a height of about 6 mm, occurs with a light green color (144B). The style has a color of 63B on the top and 2D on the bottom. There are about 500 stamens per flower that are about 14 mm long with color 2D. Anthesis, in the location where the plants are grown, peaks in May and June depending on the weather but some anthesis occurs as late as November. The flowers are not pollinated by honey bees but rather by a specialized cactus bee that makes its nest in holes in the ground.

In Table 1 can be found a comparison of the means and 95% confidence intervals for 93 analyses of Texas A&M 1281 which is a red fruited variety, that is very similar to the commercial 'Rossa' from Italy, a Chilean green variety TX 1319 and our new green variety 'DAR 1-29-21 Green'. It is to be noted that the Brix of 12.7, fruit size of 145 grams and 55% pulp percentage for TX 1281 is similar to published values for the Rossa variety described above. Both green varieties have much greater Brix and firmness than the red commercial variety. The 'DAR 1-29-21 Green' was slightly higher in Brix than TX 1319 but lower in firmness. While both green varieties have a lower pulp % than the red type, the 'DAR 1-29-21' Green has a statistically greater pulp % than the TX 1319 from Chile.

TABLE 1

A comparison of new 'DAR 1-29-21 Green' Opuntia ficus indica with green fruit to a standard commercial red type fruit TX 1281, and a Chilean green fruited variety TX 1319.

| Variety | Number of analyses | Average of Brix (%) | 95% CI of Brix | Average of firmness (lb) | 95% CI of firmness | Average of Fruit weight (g) | 95% CI of fruit weight | Average of pulp percent (%) | 95 % CI of pulp percent |
|---|---|---|---|---|---|---|---|---|---|
| TX1319 | 144 | 14.4 | 0.14 | 3.1 | 0.08 | 152.4 | 6.4 | 47 | 1.1 |
| 'DAR 1-29-21 Green' | 77 | 14.6 | 0.13 | 2.9 | 0.09 | 150.5 | 4.5 | 50 | 1.1 |
| TX1281 | 93 | 12.7 | 0.20 | 1.9 | 0.07 | 145.5 | 4.9 | 55 | 1.2 |

In the area where these cacti are grown commercially in Gonzalez, Calif., approximately 40 km from the Pacific Ocean, the maximum daily temperatures during the growing season rarely exceed temperatures of 30 C for more than a few hours. However occasionally in the fall of the year, the orchards experience daily maximum temperatures of 35 C for several days. This abrupt change in temperature, results in some varieties, particularly green varieties without any betaxanthin or betacyanin pigments, to experience serious damage to fruit quality. In this case, the edible portion of the fruits changes from an opaque solid appearance to water soaked, translucent appearance and the flavor is no longer acceptable. This phenomenon has been denoted "clearing" by growers. This clearing was rated by cutting fruits in half and estimating the percentage of water soaked translucent aspect to the cut fruit. A 0, 1, 2, 3, 4 and 5 rating implied that approximately 0, 20, 40, 60, 80 and 100% of the surface area of edible portion was translucent. The results of the first clearing assay on 17 Oct. 2008 are presented in Table 2 and illustrate the fact that none of the colored fruits i.e. 'DAR 1-12-19 Red', 'DAR 1-21-27-Purple' or 'DAR 1-27-24 Orange' had significant clearing. It can also be observed that the 'DAR 1-29-21 Green' had significantly lower clearing than green varieties AR3 and AR7 from Argentina.

TABLE 2 clearing estimates of cactus pear fruits from the 17 Oct. 2008 Evaluation

| Number of fruits | Fruit color | Clone | Mean clearing rating (0-5) | 95% CI |
|---|---|---|---|---|
| 11 | Red | 'DAR 1-12-19' | 0.00 | 0 |
| 8 | Purple | 'DAR 1-21-27' | 0.25 | 0.32 |
| 11 | Orange | 'DAR 1-27-24' | 0.18 | 0.24 |
| 11 | Green | 'DAR 1-29-21 Green' | 0.91 | 0.49 |
| 10 | Green | 'DAR 1-29-22' | 1.00 | 0.41 |
| 13 | Green | AR3 | 3.08 | 0.84 |
| 12 | Green | AR7 | 2.83 | 0.96 |

A later clearing evaluation on 23 Oct. 2009 found that 'DAR 1-29-21 Green' had statistically lower clearing values at the 95% probability level from two green Chilean fruit varieties, TX 1319 and TX 1321 (Table 3).

TABLE 3 clearing estimates of cactus pear fruits from the 23 Oct. 2008 Evaluation.

| Number of fruits | Fruit color | Clone | Mean clearing rating (0-5) | 95% CI |
|---|---|---|---|---|
| 25 | Green | TX 1319 | 1.28 | 0.51 |
| 20 | Green | DAR 1-20-13 | 0.80 | 0.48 |
| 13 | Green | 'DAR 1-29-21 Green' | 0.23 | 0.24 |
| 16 | Green | 'DAR 1-29-22' | 0.75 | 0.46 |
| 24 | Green | TX 1321 | 1.42 | 0.61 |

With regard to seed content, the TX 1281 had 4.59 grams of seeds per 100 gram of edible pulp(with a 95% confidence interval of 0.56) while the 'DAR 1-29-21 Green' had 4.7 grams of seeds per 100 grams of pulp (with a 95% confidence interval of 0.73).

In the location where the varieties are grown in the cool coastal region of central California, normally the date of first picking is the first of October and the date of last picking is May 15. Under optimal storage conditions of refrigeration and humidity control, this non climacteric fruit has a shelf life of about 3 weeks. The plant can withstand a few hours of 20 F with the only damage being to flowers and immature cladodes. Temperatures in the Salinas Valley where the plants are grown never exceed 98 F and the plants suffer no damage from these temperatures. The plant has good vigor in producing new cladodes from March/April until late November.

The major disease is known as engrosamiento de cladodios (pad swelling) in Mexico that causes stunting of fruits and pads. Our recent research indicates this is caused by an Umbravirus that is transmitted by cowpea aphids. To date all commercial fruit type varieties are susceptible to this virus. The plant is also susceptible to damage from wild cochineal (*Dactylopius* spp) insects.

The invention claimed is:

1. A new and distinct green fruited *Opuntia ficus indica* plant named 'DAR 1-29-21 Green', substantially as illustrated and described, characterized by a lime green edible interior portion (145A, 145B 145C), and the following combination of fruit characteristics, Brix 14.6%, pulp firmness 2.9 lb, edible pulp/fruit weight 50%, and greater resistance to water soaked, translucent "clearing" resulting abrupt high temperature changes than other green fruited cactus pears.

* * * * *